United States Patent
Kollmann

(10) Patent No.: US 9,346,041 B2
(45) Date of Patent: May 24, 2016

(54) PRODUCTION OF A CATALYTICALLY ACTIVE, METALLIZED REACTIVE FOAM MATERIAL AND USE THEREOF

(76) Inventor: Wolfgang Kollmann, Wartberg (AT)

( * ) Notice: Subject to any disclaimer, the term of this patent is extended or adjusted under 35 U.S.C. 154(b) by 92 days.

(21) Appl. No.: 14/122,449

(22) PCT Filed: May 25, 2012

(86) PCT No.: PCT/EP2012/059897
§ 371 (c)(1),
(2), (4) Date: Jan. 29, 2014

(87) PCT Pub. No.: WO2012/163853
PCT Pub. Date: Dec. 6, 2012

(65) Prior Publication Data
US 2014/0179513 A1    Jun. 26, 2014

(30) Foreign Application Priority Data
May 31, 2011   (DE) .......................... 10 2011 050 758

(51) Int. Cl.
*B01J 31/38*   (2006.01)
*A61L 2/08*    (2006.01)
(Continued)

(52) U.S. Cl.
CPC .................. *B01J 31/38* (2013.01); *A61L 2/088* (2013.01); *A61L 9/205* (2013.01); *B01J 21/063* (2013.01); *B01J 23/38* (2013.01); *B01J 23/70* (2013.01); *B01J 23/72* (2013.01); *B01J 27/188* (2013.01); *B01J 27/1853* (2013.01); *B01J 31/06* (2013.01);
(Continued)

(58) Field of Classification Search
CPC ............ B05D 1/36; B05D 7/00; C23C 16/00; B01J 35/004; B01J 37/00; B01J 37/0215; B01J 37/0244; B01J 21/063; B01J 23/72; B01J 23/76; B01J 23/8926
USPC ........ 427/402, 419.1, 419.2, 421.1, 427, 435, 427/443.1, 443.2, 250; 428/689, 698, 699; 502/300, 325, 329–335, 345, 349, 350
See application file for complete search history.

(56) References Cited

U.S. PATENT DOCUMENTS

| 5,034,367 A | 7/1991 | Falke et al. |
| 5,607,743 A | 3/1997 | Disselbeck |

(Continued)

FOREIGN PATENT DOCUMENTS

| CA | 2017268 A | 11/1990 |
| DE | 3522287 A1 | 1/1987 |

(Continued)

OTHER PUBLICATIONS

"Antimicrobial activity of titania/silver and titania/copper films prepared by CVD," H. A. Foster et al. Journal of Photochemistry and Photobiology A: Chemistry 216 (2010), pp. 283-289.*

*Primary Examiner* — Patricia L Hailey
(74) *Attorney, Agent, or Firm* — Abel Law Group, LLP

(57) ABSTRACT

The invention relates to a catalytic material which is used as an optofluidic reactor, and also a method for production thereof. In this case, first a reticulated plastic foam can be fabricated which then is coated with at least one first metal or metal alloy layer. Subsequently, a photocatalytic substrate is then applied to the metal or metal alloy layer. The photocatalytic substrate eliminates bacteria, viruses and other harmful substances, as well as fine dust or fungal spores, when the optofluidic reactor is used.

4 Claims, 2 Drawing Sheets

(51) Int. Cl.

| | | |
|---|---|---|
| *B01J 21/06* | (2006.01) | |
| *B01J 23/38* | (2006.01) | |
| *B01J 23/70* | (2006.01) | |
| *B01J 27/185* | (2006.01) | |
| *B01J 31/06* | (2006.01) | |
| *B01J 35/00* | (2006.01) | |
| *B01J 37/03* | (2006.01) | |
| *B01J 37/34* | (2006.01) | |
| *B32B 15/04* | (2006.01) | |
| *C23C 28/00* | (2006.01) | |
| *E04C 2/292* | (2006.01) | |
| *A61L 9/20* | (2006.01) | |
| *C25D 5/10* | (2006.01) | |
| *C25D 5/12* | (2006.01) | |
| *C23C 18/12* | (2006.01) | |
| *B01J 23/72* | (2006.01) | |
| *B01J 27/188* | (2006.01) | |
| *B01J 23/835* | (2006.01) | |
| *B01J 37/02* | (2006.01) | |

(52) U.S. Cl.
CPC ............ *B01J 35/004* (2013.01); *B01J 37/0244* (2013.01); *B01J 37/036* (2013.01); *B01J 37/348* (2013.01); *B32B 15/046* (2013.01); *C23C 18/1216* (2013.01); *C23C 18/1241* (2013.01); *C23C 18/1254* (2013.01); *C23C 28/30* (2013.01); *C25D 5/10* (2013.01); *C25D 5/12* (2013.01); *E04C 2/292* (2013.01); *A61L 2209/14* (2013.01); *B01J 23/835* (2013.01); *B01J 37/0225* (2013.01); *B01J 37/0238* (2013.01)

(56) References Cited

U.S. PATENT DOCUMENTS

| | | | |
|---|---|---|---|
| 6,051,117 A * | 4/2000 | Novak | C25B 9/00 204/252 |
| 6,154,311 A * | 11/2000 | Simmons, Jr. | G02B 5/208 359/350 |
| 6,180,548 B1 | 1/2001 | Taoda et al. | |
| 6,468,428 B1 | 10/2002 | Nishii et al. | |
| 6,531,100 B1 | 3/2003 | Ogata et al. | |
| 6,537,379 B1 * | 3/2003 | Vajo | C09K 3/18 134/1 |
| 8,372,477 B2 | 2/2013 | Buelow et al. | |
| 8,673,157 B2 | 3/2014 | Kolios et al. | |
| 2002/0016250 A1 * | 2/2002 | Hayakawa | C03C 17/23 502/5 |
| 2003/0050196 A1 * | 3/2003 | Hirano | A61L 9/00 507/238 |
| 2003/0118827 A1 * | 6/2003 | Pinneo | B23K 1/0008 428/408 |
| 2005/0266163 A1 * | 12/2005 | Wortman | C23C 4/02 427/248.1 |
| 2005/0266235 A1 * | 12/2005 | Nakajima | C08J 7/045 428/336 |
| 2005/0266248 A1 * | 12/2005 | Millero | C09D 5/1675 428/411.1 |
| 2008/0241573 A1 * | 10/2008 | Askin | B05D 5/08 428/613 |
| 2009/0117371 A1 | 5/2009 | Glaeser et al. | |
| 2010/0316538 A1 | 12/2010 | Buelow et al. | |
| 2011/0224066 A1 | 9/2011 | Schmidt et al. | |
| 2012/0168300 A1 | 7/2012 | Kolios et al. | |

FOREIGN PATENT DOCUMENTS

| | | | |
|---|---|---|---|
| DE | 3920428 A1 | 1/1991 | |
| DE | 10013237 A1 | 4/2002 | |
| DE | 10210465 A1 | 10/2003 | |
| DE | 69729513 T2 | 5/2005 | |
| JP | H0327145 A | 2/1991 | |
| JP | H1066878 A | 3/1998 | |
| JP | 2000084415 A | 3/2000 | |
| JP | 2000210534 A | 8/2000 | |
| JP | 2007-275292 | * 10/2007 | ............... A61L 9/01 |
| JP | 2007275292 | 10/2007 | |
| WO | 2007115796 A2 | 10/2007 | |
| WO | 2010036543 A2 | 4/2010 | |
| WO | 2011032900 A2 | 3/2011 | |

* cited by examiner

PRODUCTION OF A CATALYTICALLY ACTIVE, METALLIZED REACTIVE FOAM MATERIAL AND USE THEREOF

BACKGROUND OF THE INVENTION

1. Field of the Invention

The invention relates to an optofluidic reactor and thus a catalytic material for eliminating bacteria, viruses or fine dust and fungal spores and other harmful substances.

2. Discussion of Background Information

It is known in the art to use photocatalytic substrates as optofluidic reactors. Such a substrate is e.g. titanium dioxide ($TiO_2$)—preferably in the tetragonal, crystalline form of anatase. When irradiated with sunlight, the latter releases electrons which break up impurities or other contaminants into harmless substances. The release of electrons of the oxide and the accompanying photocatalytic reaction is composed of a number of physical and chemical processes. In essence, oxygen radicals are formed on the oxide surface by the free electrons, said radicals being also referred to as active oxygen. These oxygen radicals include free radicals, such as the hyperoxide anion, the hydroxyl radical, the peroxyl radical or alkoxyl radical, and also stable molecular radicals, such as the known oxygen peroxide, the hydroperoxide, ozone or the hypochloride anion. These oxygen radicals decompose molecules and organic pollutants when they contact the oxide surface. The activated oxygen also decomposes odorous substances and air pollutants, such as nitrogen oxides, and organic fine dust. In addition, this oxygen kills bacteria and viruses—even aggressive pathogens, such as SARS and H5N1, are effectively controlled upon contact with the oxide surface.

SUMMARY OF THE INVENTION

The object of the present invention is in particular to provide an optofluidic reactor having a high degree of efficiency. This object is a) achieved, on the one hand, by the production of a catalytic material which combines photocatalysis and a fluid flow.
b) On the other hand, this object is achieved by providing a coating in which a metal matrix having a catalytically acting metal or metal oxide is formed on the surface.

These two aspects can be advantageously combined with each other.

Ad a) For the purpose of fluid flow, a reticulated plastic foam made of polyether sulfone (PES) or polypropylene (PP) or polyethylene (PE) or polyurethane (PU) or polyester or polyether is created and is reticulated as a basic foam. During reticulation, the thin intermediate walls are partially opened between the individual foam cells so as to make the foam permeable to fluid. Such a foam has a huge surface area which, when a fluid flows through, is contacted by the latter. The fluid can be air to be cleaned or also water to be cleaned. In this respect, the optofluidic reactor is preferably used for room air or water treatment.

In order to treat water, the optofluidic reactor can be embedded between layers permeable to U.V. light, such as glass, for the purpose of protection. It is then inserted in the current gradient of a water course to be cleaned. A prefilter for filtering coarse suspended particles can be arranged upstream thereof.

Such a reticulated foam suitable for fluid flow advantageously has a pore number of up to 34 ppi (pores per inch). As an example, the pore number is 9 ppi on the average (fluctuation width from 8 to 10 ppi) or 10.5 ppi on the average (fluctuation width from 8 to 13 ppi) or 14.5 ppi on the average (fluctuation width from 12 to 17 ppi) or 19.5 ppi on the average (fluctuation width from 16 to 23 ppi) or 25.5 on the average (fluctuation width from 12 to 29 ppi) or 30.5 on the average (fluctuation width from 27 to 34 ppi).

The reticulated basic foam is then coated in a further process step with at least one first metal layer or metal alloy layer. As a result, the foam is hardened and the resulting solid composite material, e.g. in the form of plates, can be used as a ceiling member in rooms or as separating walls herein. As a result of this metal coating, embrittlement of the basic material, i.e. the foam, by light is prevented. In addition, a foam coated in such a way complies with decorative standards by a suitable selection of a metal or a metal alloy. The layer thickness of the metal is here chosen in such a way that the coated foam material acquires an inherent load-bearing capacity. This can also serve for preventing sagging or bending of the composite material if it is made as a panel. The strength of the material can be well controlled by selecting the layer thickness of the metal. It is also possible to apply several metal layers in succession. A suitable layer thickness has at least one (numeral) micrometer. While in thin foam panels a metal coating by means of vapor deposition provides good results, wet chemical coating methods are advantageous for relatively thick foam panels because the relatively thick foam can be well coated up into its center thereby.

All physically, thermally or wet-chemically depositable metals or metal alloys are suitable as coating metals.

The metal-coated foam composite is now an ideal substrate for the catalytically active layer to be applied subsequently, i.e. of the photocatalytic substrate. A suitable photocatalytic substrate used is titanium dioxide ($TiO_2$)—preferably in the tetragonal, crystalline form of anatase—or a metal layer made of copper, nickel, zinc, tin, cobalt or manganese or alloys or oxides thereof, also in admixtures of the individual oxides. A precious metal layer made of silver, palladium or platinum or of alloys and compositions thereof is also suitable as a photocatalytic substrate.

Then, an optofluidic reactor has been created which owing to its strength resulting from the at least one first metal layer can easily be cleaned with water or the like without losing its action.

The above combination of photocatalysis and fluid flow according to the invention shows a huge improvement in the efficiency of the photocatalyst. The channels produced in the foam and branching off like branches in the foam ensure a great ratio of surface area to fluid volume, and therefore the optofluidic reactor according to the invention reaches a better purification.

A preferred exemplary embodiment is described below: A reticulated plastic foam having a preferred pore number of 12-17 ppi and a thickness of 10 mm is coated in a first coating step with a copper layer having a thickness of some few nanometers to one (1 µm) or more micrometers, said copper layer being applied to the foam by vapor deposition, sputtering or electroplating. This first metal layer is then reinforced by a further layer by means of metal plating using copper, iron or aluminum having a layer thickness of more than 20 µm. A nickel, white bronze or cobalt-tin layer is applied by electroplating to this copper layer as a corrosion protection and can be combined with antiallergenic cobalt-tin metal layer. In place of this layer or combination of layers, it is also possible to apply a precious metal layer of e.g. palladium, platinum or silver or alloys thereof—also as an alloy having one of the above mentioned metals, i.e. nickel, zinc, white bronze, cobalt or tin. A layer thickness of at least 5 µm has shown to be advantageous.

The metallized material obtained by the coating is then coated with a titanium dioxide layer as a photocatalytic substrate by immersing or flow-coating the foam or spraying it thereon.

The coating is a water- or solvent-based titanium dioxide solution which is produced by the sol-gel method. In addition to the photocatalytic effect thereof, this coating is superhydrophilic, self-cleaning and strongly antimicrobial.

Interior ceiling panels or room dividers can be made of a molded body which is obtained from a material according to the above description, thus cleaning the air in a room. Design elements that can be installed in interior rooms are also advantageous to clean the room air. Here, the most diverse forms of material can be formed. In such embodiments, the sound absorption is remarkable in addition to the room air cleaning effect. For example, the interior members can be beneficially employed in open-plan offices, also to reduce noise.

For the purpose of shaping, the individual optofluidic elements, e.g. panels, can be connected with one another, e.g. be joined by adhering. Care should here be taken that sufficient U.V. light can penetrate into the center of the thus connected elements and a flow is ensured.

A reactor made of members between which a UV lamp is embedded has proved to be advantageous. Said lamp radiates UV light from the center of the reactor outwards. In addition to the emitted UV light, the lamp involved can additionally radiate light in the visible range, and therefore such a reactor then also serves as a light. As a result of the thus obtained convection of the lamp, a lamp involved in this way also leads to a compulsory flushing of the optofluidic reactor by the resulting heat.

According to the invention there is also comprised a ventilation unit which as an essential functional element has an optofluidic reactor as described above. Such a ventilation unit has a ventilator or the like to force air through the optofluidic reactor. This compulsory flushing of the photocatalytic reactor increases the cleaning effect of the air many times over. In an advantageous way, the foam material according to the invention as an optofluidic reactor in such a ventilation unit can readily be exchanged, i.e. disassembled, and also be cleaned.

The optofluidic reactor according to the invention can also be used advantageously as a filter body for air suction hoods. They are used in the art for kitchens or for evacuating fumes, e.g. solvents, welding fumes or smoke gases.

As already shown above, the photocatalytic effect of the optofluidic reactor can be advantageously increased if it is irradiated by a UV-A lamp. An advantageous embodiment of the ventilation unit, the air suction hood or the interior shaped body thus has a UV-A lamp serving for then irradiating the optofluidic reactor as needed. It is thus also suitable to form a design body made of a metallized foam material according to the invention that is irradiated with such a UV lamp.

BRIEF DESCRIPTION OF THE DRAWINGS

Attached FIG. 2 is an enlarged view of the foam from FIG. 1.

Figure 1:
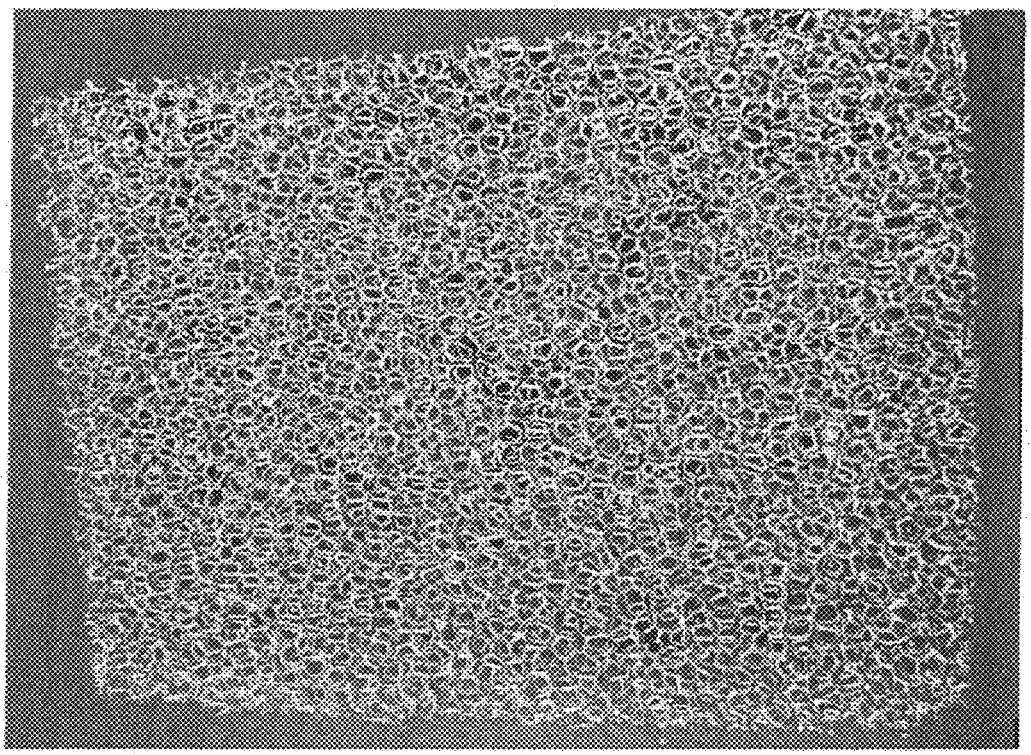
FIGS. 1 and 2 are photographs of a reticulated basic foam as can be used as an initial material for the optofluidic reactor.
Figure 2:
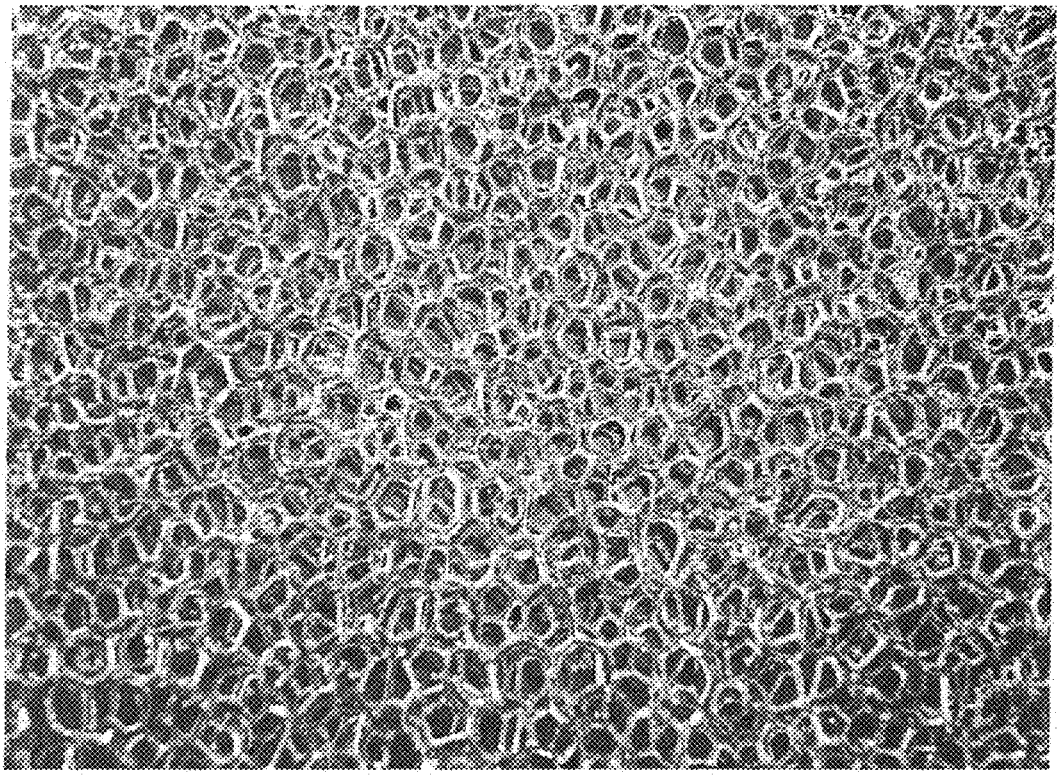

With respect to solution variant b), according to which a metal matrix is formed on a surface, a new coating is shown below, which serves for decontamination from bacteria, viruses and other general impurities. Along with a coating for a reticulated basic foam, as described above and explained for the most diverse applications, there are additionally also coating applications without fluid flushing, such as for door knobs, sanitary fittings, or for all surfaces which are contacted and are thus exposed to contamination with bacteria and viruses. This concerns applications in private households, hospitals or public institutions.

It is known to disperse in electroplating electrolytes different substances, such as diamond dust, SiC, $Al_2O_3$, CBN, WC, TiC, PTFE or graphite and deposit them with the respective electrolyte by electroplating (e.g. sulfamate nickel, Watts sulfate nickel or the like) or externally currentless (e.g. chemical nickel) on a respective component to reduce wear, increase the temperature resistance or improve the sliding properties.

According to the present invention, $TiO_2$—preferably in the anatase form—is made for use as a photocatalytically active dispersion layer as a so-called TiO2-metal matrix layer.

The preferred particle size of $TiO_2$ is 0-3 μm; e.g. KRONOClean 7000 and KRONOClean 7050.

It is also possible to use nanoscale $TiO_2$ particles having a size of about 20 nm, wherein on account of conglomeration problems the production of the suspension can be complicated but is feasible. In connection with the nanoscale particles it is useful to employ dispersing chemicals as an aid.

The basic process of the coating procedure using e.g. $TiO_2$—ENiP ($TiO_2$ with chemical nickel-phosphorus metal layer) or electroplated NiP is described below for the reticulated foam for cleaning air and water, and described also in connection with plastic components:

1. The reticulated foam is coated in a first coating step preferably with a copper layer of >1 μm by vapor deposition or by an externally currentless method (chemical copper).

2. This first metal layer is coated with copper, iron or aluminum (preferably Cu) having a layer thickness of more than 10 μm by electroplating until the foam obtains inherent rigidity.

3. Another metal layer or metal alloy layer, e.g. Ni, white bronze, yellow bronze, NiP, Cr, NiKo, ENiCoP, having a layer thickness of >5 μm is applied to this layer.

4. The photocatalytic, e.g. NiP—$TiO_2$, layer having a layer thickness of >1 μm is applied to this layer.

It is also possible to apply a Cu—$TiO_2$ layer having a layer thickness of >1 μm to the first metal layer produced according to point 2.

According to an embodiment it is possible to apply the photocatalytic layer directly to the copper layer 2 without any further intermediate layer.

According to an embodiment, it is also possible to apply to the photocatalytic layer 4 a layer, e.g. bright chrome, or a precious metal, e.g. Au, Pd, Rt or Pt. In the case of metallic workpieces, step 1 is omitted.

Exemplary embodiment for producing an electrolyte for forming a metal matrix having a TiO2-Ni deposition according to step 4:

Watts (sulfate) nickel electrolyte having the composition of

| | |
|---|---|
| NiSO4•6H2O | 350 g/l |
| NiCl2•6H2O | 45 g/l |
| H3BO3 | 45 g/l |
| T | 55° C. |
| pH | 4 |
| TiO2 | 20-150 g/l particle size 0-3 μm |
| Cathodic current density | 5 A/dm2 |
| Cation active fluorosurfactant | 0.2 g/l FT 248 (BASF company) |

An incorporation rate of up to 50% by mass is possible by means of this composition.

According to an embodiment, it is also possible to use a wetting agent, such as sodium dodecyl sulfate, or a standard wetting agent from galvanochemical supply firms to prevent the formation of pores.

The $TiO_2$ particles are kept suspended by an electrolyte movement by means of mechanical stirring. A mild introduction of air is advantageous.

The respective precise $TiO_2$ concentration depends on the desired incorporation rate of the oxide and the component geometry as well as generally the component (surface roughness, microgeometry, etc.).

The stirring rate and the applied current density also have an essential influence on the incorporation rate depending on the component geometry and the indicated microstructure.

What is essential is also to accurately maintain the pH value since as a result of the production of the $TiO_2$ particles to be incorporated residues of e.g. precursor substances can still adhere (alkaline and acidic). The $TiO_2$ metal matrix deposition is possible with diverse electrolytes as a matrix metal.

Suitable matrix metals which are employed and produced by electroplating (with current) are NiP, Ni, Co, Cu, W, Mn, Mo, Cr, Sn, Zn (hard chrome), precious metals, such as Pd, Pt, ruthenium, rhodium and the different alloys thereof. Sulfamate electrolytes or ionic liquids can also be used.

Also suitable is the matrix metal with externally currentless methods such as chemical nickel-phosphorus and diverse alloys, e.g. Ni—Co—P (hydrazine reducing agent), Co—P, Ni—Cu—P, Ni—W—P, Ni—Mo—P and chemical copper.

The major advantage of these $TiO_2$ incorporation layers is that the catalytically active particles are firmly fixed in a highly wear-resistant metal matrix and hence a very long duration of action has to be expected.

In addition, there are always new $TiO_2$ particles exposed on the surface at any point in time even with an occurring wear of the coating and thus take effect until the coating is fully worn. In contrast to coatings applied in the sol-gel method, painting method, (wet, coating powder) or thin-film method (sputtering, vapor deposition, etc.), these coating of a metal matrix last incomparably longer and thus make them predestined for components and surfaces under abrading conditions which are frequently under the stress of touch, for example, and e.g. in particular in hospitals contaminated with different bacteria and viruses.

$TiO_2$ metal matrix layers made in this way have a major advantage that they continuously destroy viruses and bacteria on door knobs, gripping surfaces, etc. in the presence of light and thus there is utmost protection from infection and transmissions of diseases by contact contamination, also beyond cleaning cycles.

The introduction of $TiO_2$ particles into the environment is thus minimized over less wear-resistant paint layers.

By means of the described procedural method it is also possible to coat metallized, textile base materials such as fleeces, fabrics and the like made of plastic, glass or carbon base material.

What is claimed is:

1. A method of producing a catalytic material for eliminating contaminants, wherein the method comprises:
    (a) providing a panel made of reticulated plastic foam having a thickness of at least 10 mm;
    (b) applying two copper layers on a surface of the panel of (a);
    (c) applying a photocatalytic $TiO_2$ substrate in a sol-gel method from solution by immersion, flow-coating or spraying;
    and wherein after (b) and before (c) a further metal layer of aluminum, nickel, tin, zinc, silver, palladium, platinum, or alloys thereof is applied.

2. The method of claim 1, wherein the metal of the further metal layer is selected from nickel, tin, silver, or alloys thereof.

3. A catalytic material for eliminating contaminants, wherein the material comprises:
    (a) a panel made of reticulated plastic foam having a thickness of at least 10 mm;
    (b) two copper layers on a surface of the panel (a);
    (c) a photocatalytic $TiO_2$ substrate applied in a sol-gel method from solution by immersion, flow-coating or spraying;
    and wherein a further metal layer made of aluminum, nickel, tin, zinc, silver, palladium, platinum, or alloys thereof is present between (b) and (c).

4. The catalytic material of claim 3, wherein a metal of the further metal layer is selected from nickel, tin, silver, and alloys thereof.

* * * * *